United States Patent
Rapoport et al.

(10) Patent No.: US 10,444,170 B2
(45) Date of Patent: Oct. 15, 2019

(54) SYSTEM AND METHOD FOR ANALYSIS OF FLUIDS FLOWING IN A CONDUIT

(71) Applicant: Aspect AI Ltd., Shoham (IL)

(72) Inventors: Uri Rapoport, Moshav Ben Shemen (IL); Boaz Shapira, Echhar (IL)

(73) Assignee: ASPECT AI LTD., Shoham (IL)

( * ) Notice: Subject to any disclaimer, the term of this patent is extended or adjusted under 35 U.S.C. 154(b) by 81 days.

(21) Appl. No.: 15/740,098

(22) PCT Filed: Jul. 3, 2016

(86) PCT No.: PCT/IL2016/050711
§ 371 (c)(1),
(2) Date: Dec. 27, 2017

(87) PCT Pub. No.: WO2017/002126
PCT Pub. Date: Jan. 5, 2017

(65) Prior Publication Data
US 2018/0188194 A1    Jul. 5, 2018

Related U.S. Application Data

(60) Provisional application No. 62/187,822, filed on Jul. 2, 2015.

(51) Int. Cl.
*G01N 24/08* (2006.01)
*G01R 33/483* (2006.01)
*G01R 33/563* (2006.01)

(52) U.S. Cl.
CPC ......... *G01N 24/081* (2013.01); *G01N 24/085* (2013.01); *G01R 33/4835* (2013.01); *G01R 33/563* (2013.01)

(58) Field of Classification Search
CPC ............... G01N 24/081; G01N 24/085; G01R 33/4835; G01R 33/563
See application file for complete search history.

(56) References Cited

U.S. PATENT DOCUMENTS 2,768,529 A    10/1956    Hagler, Sr.
3,175,403 A    3/1965    Nelson
(Continued)

FOREIGN PATENT DOCUMENTS

CN    1236478    11/1999
CN    1291873    4/2001
(Continued)

OTHER PUBLICATIONS

ANSI/ISA SP76.00.2002 Miniature, Modular Mechanical Standard Specifications, 2002.
(Continued)

*Primary Examiner* — G. M. A Hyder
(74) *Attorney, Agent, or Firm* — Pearl Cohen Zedek Latzer Baratz LLP

(57) ABSTRACT

System and method for analyzing changes in a fluid flowing through a conduit, including defining at least one coordinate within said conduit, said conduit having a first plurality of slices, receiving at least one known value for at least one property of the fluid, measuring said fluid using magnetic resonance, determining at least one image from the measured fluid, the at least one image having a second plurality of slices for said at least one coordinate, determining a second set of values for said at least one property of said fluid, comparing the first set of values and second set of values for said at least one property to determine a difference value, checking deviation of the determined difference from a predetermined value for said fluid, and issuing an alert if the deviation is not substantially zero.

20 Claims, 5 Drawing Sheets

(56) References Cited

U.S. PATENT DOCUMENTS

| | | |
|---|---|---|
| 3,989,630 A | 11/1976 | Walker |
| 4,417,474 A | 11/1983 | Elderton |
| 4,468,622 A | 8/1984 | Frese et al. |
| 4,697,594 A | 10/1987 | Mayo, Jr. |
| 4,904,603 A | 2/1990 | Jones et al. |
| 4,994,746 A | 2/1991 | Panosh |
| 5,023,551 A | 6/1991 | Kleinberg et al. |
| 5,145,189 A | 9/1992 | Pope |
| 5,161,409 A | 11/1992 | Hughes et al. |
| 5,168,226 A | 12/1992 | Hinks |
| 5,208,534 A | 5/1993 | Okamoto et al. |
| 5,280,243 A | 1/1994 | Miler |
| 5,306,909 A | 4/1994 | Jones et al. |
| 5,479,925 A | 1/1996 | Dumoulin et al. |
| 5,532,593 A | 7/1996 | Maneval et al. |
| 5,557,103 A | 9/1996 | Hughes et al. |
| 5,557,201 A | 9/1996 | Kleinberg et al. |
| 5,696,448 A | 12/1997 | Coates et al. |
| 5,705,927 A | 1/1998 | Sezginer et al. |
| 5,757,187 A | 5/1998 | Wollin |
| 5,784,333 A | 7/1998 | Tang et al. |
| 5,827,952 A | 10/1998 | Mansure et al. |
| 5,986,454 A | 11/1999 | Leifer |
| 6,069,106 A | 5/2000 | Hettinger, Jr. |
| 6,090,728 A | 7/2000 | Yenni, Jr. et al. |
| 6,107,796 A | 8/2000 | Prammer |
| 6,178,807 B1 | 1/2001 | Baldwin et al. |
| 6,215,304 B1 | 4/2001 | Slade |
| 6,268,726 B1 | 7/2001 | Prammer et al. |
| 6,362,619 B2 | 3/2002 | Prammer et al. |
| 6,412,337 B1 | 7/2002 | Arzate et al. |
| 6,421,337 B1 | 7/2002 | Rao et al. |
| 6,452,390 B1 | 9/2002 | Wollin |
| 6,507,191 B1 | 1/2003 | Eguchi et al. |
| 6,518,758 B1 | 2/2003 | Speier et al. |
| 6,549,007 B1 | 4/2003 | Hills et al. |
| 6,550,327 B1 | 4/2003 | Van Berk |
| 6,646,437 B1 | 11/2003 | Chitale et al. |
| 6,807,857 B2 | 10/2004 | Storm, Jr. et al. |
| 6,856,132 B2 | 2/2005 | Appel et al. |
| 6,907,375 B2 | 6/2005 | Guggari et al. |
| 6,913,827 B2 | 7/2005 | George et al. |
| 6,952,096 B2 | 10/2005 | Freedman |
| 7,075,366 B2 | 7/2006 | Deem et al. |
| 7,295,933 B2 | 11/2007 | Gysling et al. |
| 7,352,179 B2 | 4/2008 | Chen et al. |
| 7,486,071 B2 | 2/2009 | Care et al. |
| 7,489,132 B2 | 2/2009 | Arik et al. |
| 7,570,058 B1 | 8/2009 | Wong et al. |
| 7,823,656 B1 | 11/2010 | Williams |
| 7,908,034 B2 | 3/2011 | Gray |
| 7,921,731 B2 | 4/2011 | Bajikar et al. |
| 8,024,962 B2 | 9/2011 | Tonmukayakul et al. |
| 8,143,887 B2 | 3/2012 | Pusiol |
| 8,256,532 B2 | 9/2012 | Gray |
| 8,373,412 B2 | 2/2013 | Kruspe et al. |
| 8,461,842 B2 | 6/2013 | Thuringer et al. |
| 8,469,118 B2 | 6/2013 | Passade-Boupat et al. |
| 8,736,263 B2 | 5/2014 | Minh |
| 8,763,170 B1 | 7/2014 | Ungarsohn |
| 8,763,710 B2 | 7/2014 | Graue |
| 8,791,695 B2 | 7/2014 | Balcom et al. |
| 8,807,084 B2 | 8/2014 | Rapoport et al. |
| 8,812,236 B1 | 8/2014 | Freeman et al. |
| 8,851,018 B2 | 10/2014 | Rapoport et al. |
| 8,896,310 B2 | 11/2014 | Rapoport |
| 9,194,972 B2 | 11/2015 | Van Der Zwaag et al. |
| 9,448,093 B2 | 9/2016 | Rapoport |
| 9,476,847 B2 | 10/2016 | Trygstad et al. |
| 2002/0173717 A1 | 11/2002 | Rohling et al. |
| 2003/0006768 A1 | 1/2003 | Kleinberg et al. |
| 2004/0017193 A1 | 1/2004 | Speier |
| 2004/0090230 A1 | 5/2004 | Appel et al. |
| 2004/0116799 A1 | 6/2004 | Srinivasan |
| 2004/0127786 A1 | 7/2004 | Schmit et al. |
| 2004/0140800 A1 | 7/2004 | Madio et al. |
| 2004/0169512 A1 | 9/2004 | Jara |
| 2005/0011283 A1 | 1/2005 | Gysling et al. |
| 2005/0024053 A1 | 2/2005 | Care et al. |
| 2005/0030020 A1 | 2/2005 | Siess et al. |
| 2005/0044957 A1 | 3/2005 | Muldowney |
| 2005/0203420 A1 | 9/2005 | Kleen et al. |
| 2006/0011547 A1 | 1/2006 | Bell |
| 2006/0279283 A1 | 12/2006 | Nistler et al. |
| 2007/0061081 A1 | 3/2007 | Moran |
| 2007/0164737 A1 | 7/2007 | Pusiol |
| 2007/0188172 A1 | 8/2007 | Garwood et al. |
| 2008/0136049 A1 | 6/2008 | Yang et al. |
| 2008/0136409 A1 | 6/2008 | Sen et al. |
| 2008/0174309 A1 | 7/2008 | Pusiol et al. |
| 2008/0180226 A1 | 7/2008 | Schmidt |
| 2008/0189456 A1 | 8/2008 | Schmidt et al. |
| 2008/0257413 A1 | 10/2008 | Noureldin et al. |
| 2009/0004748 A1 | 1/2009 | Ganesan |
| 2009/0044638 A1 | 2/2009 | Gysling et al. |
| 2009/0050318 A1 | 2/2009 | Kasevich |
| 2009/0050369 A1 | 2/2009 | Pop et al. |
| 2009/0072824 A1 | 3/2009 | Romero |
| 2009/0090504 A1 | 4/2009 | Weightman et al. |
| 2009/0194330 A1 | 8/2009 | Gray |
| 2009/0312963 A1 | 12/2009 | Najim Al-Khamis |
| 2009/0312964 A1 | 12/2009 | Najim Al-Khamis |
| 2010/0133488 A1 | 6/2010 | Giakos |
| 2010/0154325 A1 | 6/2010 | Boesel et al. |
| 2010/0264914 A1 | 10/2010 | Minh |
| 2010/0271019 A1 | 10/2010 | Anand et al. |
| 2011/0036584 A1 | 2/2011 | Weightman et al. |
| 2011/0125333 A1 | 5/2011 | Gray |
| 2011/0162652 A1 | 7/2011 | Rapoport |
| 2011/0185795 A1 | 8/2011 | Colquhoun |
| 2011/0186049 A1 | 8/2011 | Rapoport |
| 2011/0234347 A1 | 9/2011 | Rapoport |
| 2011/0270525 A1 | 11/2011 | Hunter |
| 2011/0296911 A1 | 12/2011 | Moore et al. |
| 2011/0304333 A1 | 12/2011 | Rapoport |
| 2012/0013335 A1 | 1/2012 | Saasen et al. |
| 2012/0024602 A1 | 2/2012 | Larson |
| 2012/0065491 A1 | 3/2012 | Borgert et al. |
| 2012/0071745 A1 | 3/2012 | Rapoport |
| 2012/0073511 A1 | 3/2012 | Rapoport et al. |
| 2012/0077707 A1 | 3/2012 | Rapoport |
| 2012/0092007 A1 | 4/2012 | Li et al. |
| 2012/0119742 A1 | 5/2012 | Rapoport |
| 2012/0205288 A1 | 8/2012 | Jia et al. |
| 2012/0212224 A1 | 8/2012 | Burns |
| 2012/0265050 A1 | 10/2012 | Wang |
| 2013/0009959 A1 | 1/2013 | Calamante et al. |
| 2013/0025062 A1 | 1/2013 | Esch |
| 2013/0060474 A1 | 3/2013 | Venkataramanan et al. |
| 2013/0079624 A1 | 3/2013 | Rapoport |
| 2013/0090855 A1 | 4/2013 | Rasmus et al. |
| 2013/0091941 A1 | 4/2013 | Huh et al. |
| 2013/0109956 A1 | 5/2013 | Rapoport |
| 2013/0123639 A1 | 5/2013 | Ando |
| 2013/0124106 A1 | 5/2013 | Rogel et al. |
| 2013/0154644 A1 | 6/2013 | Virtanen et al. |
| 2013/0179092 A1 | 7/2013 | Martin et al. |
| 2013/0237803 A1 | 9/2013 | Rapoport |
| 2013/0271135 A1 | 10/2013 | Ozen et al. |
| 2013/0328559 A1 | 12/2013 | Rapoport |
| 2013/0328560 A1 | 12/2013 | Rapoport |
| 2013/0328563 A1 | 12/2013 | Rapoport |
| 2013/0345994 A1 | 12/2013 | Wiklund et al. |
| 2014/0049257 A1* | 2/2014 | Rapoport ............... G01F 1/716 324/306 |
| 2014/0050824 A1 | 2/2014 | Rapoport |
| 2014/0050827 A1 | 2/2014 | Rapoport |
| 2014/0051973 A1 | 2/2014 | Rapoport et al. |
| 2014/0051974 A1 | 2/2014 | Rapoport et al. |
| 2014/0051976 A1 | 2/2014 | Rapoport et al. |
| 2014/0099010 A1 | 4/2014 | Rapoport |
| 2014/0103927 A1 | 4/2014 | Rapoport |
| 2014/0117989 A1 | 5/2014 | Rapoport |
| 2014/0128725 A1 | 5/2014 | Rapoport |

(56) References Cited

U.S. PATENT DOCUMENTS

| | | |
|---|---|---|
| 2014/0139216 A1 | 5/2014 | Rapoport |
| 2014/0142914 A1 | 5/2014 | Rapoport |
| 2014/0152302 A1 | 6/2014 | Rapoport et al. |
| 2014/0152310 A1 | 6/2014 | Rapoport |
| 2014/0158062 A1 | 6/2014 | Rapoport et al. |
| 2014/0230850 A1 | 8/2014 | Rapoport |
| 2014/0253116 A1 | 9/2014 | Freedman et al. |
| 2014/0257081 A1 | 9/2014 | Rapoport |
| 2014/0262957 A1 | 9/2014 | Gong et al. |
| 2014/0266203 A1 | 9/2014 | Rapoport |
| 2014/0300358 A1 | 10/2014 | Rapoport |
| 2014/0309951 A1 | 10/2014 | Alvarez Vallejos et al. |
| 2014/0333304 A1 | 11/2014 | Jensen |
| 2014/0354299 A1* | 12/2014 | Rapoport .............. G01N 22/04 324/633 |
| 2014/0378821 A1 | 12/2014 | Rapoport et al. |
| 2014/0378825 A1 | 12/2014 | Rapoport et al. |
| 2015/0059157 A1 | 3/2015 | Rapoport |
| 2015/0059655 A1 | 3/2015 | Rapoport |
| 2015/0065788 A1 | 3/2015 | Rapoport |
| 2015/0084630 A1 | 3/2015 | Rapoport |
| 2015/0087051 A1 | 3/2015 | Rapoport |
| 2015/0112186 A1 | 4/2015 | Rapoport et al. |
| 2015/0130460 A1 | 5/2015 | Valori et al. |
| 2015/0137812 A1 | 5/2015 | Rapoport |
| 2015/0141799 A1 | 5/2015 | Rapoport et al. |
| 2015/0168519 A1 | 6/2015 | Rapoport |
| 2015/0268374 A1 | 9/2015 | Rapoport |
| 2015/0320888 A1 | 11/2015 | Yoneda et al. |
| 2015/0357694 A1 | 12/2015 | Denis et al. |
| 2015/0377998 A1 | 12/2015 | Bendel |
| 2016/0053187 A1 | 2/2016 | Hayasaka et al. |
| 2016/0108687 A1 | 4/2016 | Rapoport |
| 2016/0109539 A1 | 4/2016 | Mardor et al. |
| 2017/0243681 A1 | 8/2017 | Somerkoski et al. |

FOREIGN PATENT DOCUMENTS

| | | |
|---|---|---|
| CN | 1422324 | 6/2003 |
| CN | 1427877 | 7/2003 |
| CN | 1590994 | 3/2005 |
| CN | 101421636 | 4/2009 |
| CN | 101556234 | 10/2009 |
| CN | 101581717 | 11/2009 |
| CN | 101632584 | 1/2010 |
| CN | 101793147 | 8/2010 |
| CN | 101907586 | 12/2010 |
| CN | 103217362 | 7/2013 |
| CN | 103542899 | 1/2014 |
| CN | 103712071 | 4/2014 |
| CN | 103954639 | 7/2014 |
| DE | 202014105273 | 11/2014 |
| EP | 0 210 289 | 2/1987 |
| EP | 0770660 | 5/1997 |
| EP | 0835463 | 8/2003 |
| EP | 1532460 | 5/2005 |
| EP | 2604996 | 6/2013 |
| EP | 2927420 A2 | 10/2015 |
| EP | 2927420 A3 | 2/2016 |
| GB | 2341685 A | 7/1999 |
| RU | 2229023 | 5/2004 |
| RU | 2285119 | 10/2006 |
| RU | 2367982 | 9/2009 |
| SU | 876954 | 10/1981 |
| SU | 1041677 | 9/1983 |
| WO | WO1995018387 | 7/1995 |
| WO | WO2001002832 | 1/2001 |
| WO | WO2001051588 | 7/2001 |
| WO | WO2001051589 | 7/2001 |
| WO | WO2008008447 | 1/2008 |
| WO | WO2008043373 | 4/2008 |
| WO | WO2010000055 | 1/2010 |
| WO | WO2011095600 | 8/2011 |
| WO | WO2012004797 | 1/2012 |
| WO | WO2013009299 | 1/2013 |
| WO | WO2013162400 | 10/2013 |
| WO | WO2013179092 | 12/2013 |
| WO | WO2014004573 | 1/2014 |
| WO | WO2014203245 | 12/2014 |
| WO | WO2015070872 | 5/2015 |

OTHER PUBLICATIONS

Arola et al., Use of nuclear magnetic resonance imaging as a viscometer for process monitoring, Chemical Engineering Science, 1997, 52(13), 2049-2057.

Bennett, et al. A nondestructive technique for determining thermal properties of thermal barrier coatings, Journal of Applied Physics, 2005, 97, 013520,1-12.

Bird et al. Transport Phenomena, Chapter. 2, Shell momentum balances and velocity distributions in laminar flow, Dec. 31, 2002, XP-002768172, Wiley, p. 54.

Caprihan, et al. Flow measurements by NMR, Physics Reports, (Review Section of Physics Letters)1990, 198, No. 4, 195-235.

Coussot et al., Rheological behavior of drilling muds, characterization using MRI visualization, Oil & Gas Science and Technology, Rev. IFP, 2004, vol. 59, No. 1, 23-29.

Degre et al., Rheology of complex fluids by particle image velocimetry in microchannels, Appl. Phys. Lett. 89(2), 024104, 2006, 1-3.

Doble et al., Optimization of the relaxivity of MRI contrast agents: effects of poly(ethylene glycol) chains on the water-exchange rates of Gd complexes, J. Am. Chem. Soc. 2001, 123, 10758-10759.

Dogan et al., Measurement of polymer melt rheology using ultrasonics-based in-line rheometry, Meas. Sci. Technol.,2005, 16(8):1684-1690.

Dyverfeldt et al., Quantification of intravoxel velocity standard deviation and turbulence intensity by generalizing phase-contrast MRI, Magnetic Resonance in Medicine, 2006, 56:850-858.

Felemban, et al. RFID for Oil and Gas Industry: Applications and Challenges, International Journal of Engineering and Innovative Technology (IJEIT) vol. 3, Issue 5, Nov. 2013, 20-85.

Goloshevsky et al., Nuclear magnetic resonance imaging for viscosity measurements of non-Newtonian fluids using a miniaturized RF coil, Meas. Sci. Technol., 2005, 16:513-518.

Gunnerod et al., Highly automated drilling fluids system improves HSE and efficiency, reduced personnel needs, Drilling Contractor, Heath, Safety & Environment, Jan./Feb. 2009, 73-77.

Guzel et al., Predicting laminar—turbulent transition in Poiseuille pipe flow for non-Newtonian fluids, Chemical Engineering Science 2009, 64 (2) 254-264.

Hou et al., Review Article, Instrument techniques for rheometry, Review of Scientific Instruments, 2005, 76, 101101, 1-19.

Hsu et al., Encoding to the longitudinal magnetization for MR imaging and flow velocity mapping, Journal of Magnetic Resonance, 2006, 183,41-49.

International Electromechanical Commission in publication, IEC 62339-1:2006, 2006.

Kose, Katsumi, Visualization of local shearing motion in turbulent fluids using echo-planar imaging, Journal of Magnetic Resonance, 1992, 96, 596-603.

Lucas et al., An Iterative Image Registration Technique with an Application to Stereo Vision, Proceedings of Imaging Understanding Workshop, pp. 121-130 (1981).

MacGowan et al., Fast measurements of the motion and velocity spectrum of blood using MR tagging, Magnetic Resonance in Medicine, 2001, 45:461-469.

Ocali et al., Ultimate intrinsic signal-to-noise ratio in MRI, MRM, 1998, 39:462-473.

Pohost et al., Nuclear magnetic resonance imaging: With or without nuclear?, JACC Mar. 1986, vol. 7, No. 3, 709-710.

Poole et al., Development-Length Requirements for Fully Developed Laminar Pipe Flow of Inelastic Non-Newtonian Liquids, Journal of Fluids Engineering, Oct. 2007, vol. 129, 1281-1287.

Poulichet et al., Optimisation and realisation of a portable NMR apparatus and Micro Antenna for NMR, DTIP, May 2011, 11-13, Aix-en-Provence, France.

(56) References Cited

OTHER PUBLICATIONS

Prammer et al., The magnetic resonance while-drilling tool: theory and operation, Society of Engineers, 2000, SPE62981, 1-8.
Rabideau et al., The extrusion of a model yield stress fluid imaged by MRI velocimetry, J. Non-Newtonian Fluid Mech, 2010, 165, 394-408.
Shadday Jr., M.A., Recommendations for rheological testing and modelling of DWPF meter feed slurries (U), Engineering & Materials Technology Dept., WSRC-TR-94-0357, 1994 pp. 1-45.
Bradley Jr. et al., The appearance of rapidly flowing blood on magnetic resonance images, AJR, Dec. 1984, 143:1167-1174.
Yan, Jienian, Drilling Fluids Technology, May 31, 2001, China University of Petroleum Press, pp. 61-66.

* cited by examiner

```
┌─────────────────────────────────────────────┐
│ Defining at least one coordinate within a   │
│ conduit, said conduit having a first        │
│ plurality of slices                         │
└─────────────────────────────────────────────┘
                    101
                     ↓
┌─────────────────────────────────────────────┐
│ Receiving at least one known value for at   │
│ least one property of the fluid, for at     │
│ least one slice of the plurality of slices  │
│ and for the at least one coordinate         │
└─────────────────────────────────────────────┘
                    102
                     ↓
┌─────────────────────────────────────────────┐
│ Measuring the fluid using magnetic resonance│
└─────────────────────────────────────────────┘
                    103
                     ↓
┌─────────────────────────────────────────────┐
│ Determining at least one image from the     │
│ measured fluid, the at least one image      │
│ having a second plurality of slices for the │
│ at least one coordinate                     │
└─────────────────────────────────────────────┘
                    104
                     ↓
┌─────────────────────────────────────────────┐
│ Determining, from the image, a second set   │
│ of values for the at least one property of  │
│ the fluid in at least one slice of the      │
│ second plurality of slices for the at       │
│ least one coordinate                        │
└─────────────────────────────────────────────┘
                    105
                     ↓
```

Fig. 1A

SYSTEM AND METHOD FOR ANALYSIS OF FLUIDS FLOWING IN A CONDUIT

CROSS-REFERENCE TO RELATED APPLICATIONS

This application is a National Phase Application of PCT International Application No. PCT/IL2016/050711, International Filing Date Jul. 3, 2016, which claims the benefit of and priority to U.S. Provisional Patent Application No. 62/187,822, filed Jul. 2, 2015, all of which are hereby incorporated by reference in their entireties.

FIELD OF THE INVENTION

Generally, the present invention relates to analysis of fluids flowing in a conduit. More particularly, the present invention relates to systems and methods for measuring and monitoring physical and/or chemical properties of fluids flowing in a conduit, using magnetic resonance devices.

BACKGROUND OF THE INVENTION

Complex fluids are typically composed of several non-homogeneously mixed components. These fluids are often homogeneous at macroscopic scales but can be disordered at microscopic scales and can possess structures of mesoscopic length scales, which can play a key role in determining the usually quite intricate properties of the fluid. The measurement and/or analysis of complex fluid flow behavior can provide valuable insight into physical and/or chemical properties of various substances. Fluid flow analysis can be an important way to control and/or optimize industrial processes such as, for example, exploratory oilfield drilling, fluid transport and/or food production. Fluid flow analysis can also provide a diagnostic tool to various diseases such as, for example, cardiovascular diseases and/or multiple sclerosis.

Nuclear magnetic resonance imaging has wide application in fluid analysis because it can be highly-sensitive, non-invasive and/or can allow quantifying a large range of physical and/or chemical properties. Some extremely effective analytic applications can be based on the combination of pulsed field gradient spin-echo and magnetic resonance imaging experiments. These applications can rely upon fluid data collected under conditions of different flow regimes, including, for example, laminar, turbulent, and/or transient (between laminar to turbulent) flow.

SUMMARY OF THE INVENTION

Advantages of the invention can include, an ability to provide real-time information regarding fluid flowing through a conduit. Advantages of the invention can also include, an ability to measure a fluid flowing through a conduit, without interrupting an industrial processes involving the fluid.

Advantages of the invention can additionally include, an ability to provide real-time information regarding changes in properties of a fluid flowing through a conduit. Advantages of the invention can also include, an ability to measure a fluid flowing through a conduit in a predetermined location within the conduit. Other advantages include, significant cost savings due to the real-time information provided. Other advantages include, for example, accurate control on the process and/or the ability to manipulate the process with improvement of the yield, and /or stability of the process.

In one aspect, the invention involves a method of analyzing changes in a fluid flowing through a conduit. The method involves defining at least one coordinate within said conduit, said conduit having a first plurality of slices. The method also involves receiving at least one known value for at least one property of the fluid, for at least one slice of the plurality of slices and for said at least one coordinate and measuring said fluid using magnetic resonance. The method also involves determining at least one image from the measured fluid, the at least one image having a second plurality of slices for said at least one coordinate. The method also involves determining, from said image, a second set of values for said at least one property of said fluid in at least one slice of said second plurality of slices for said at least one coordinate. The method also involves comparing, at said predefined at least one slice and said at least one coordinate, the first set of values and second set of values for said at least one property to determine a difference value. The method also involves checking deviation of the determined difference from a predetermined value for said fluid and issuing an alert if the deviation is not substantially zero.

In some embodiments, the at least one coordinate is one-dimensional. In some embodiments, the at least one coordinate is two-dimensional. In some embodiments, the at least one coordinate is three-dimensional.

In some embodiments, known values for the at least one property of the fluid are received from at least one of an external database and a user. In some embodiments, the measuring of said fluid using magnetic resonance is carried out with magnetic resonance imaging.

In some embodiments, the first plurality of slices is equal to the second plurality of slices. In some embodiments, the first plurality of slices is different from the second plurality of slices. In some embodiments, at least one coordinate is received from at least one of an external database and a user. In some embodiments, a plurality of 'c' coordinates is defined, wherein a plurality of 's' slices is defined, and wherein 'c' and 's' are integers, each of which is greater than one.

In some embodiments, the obtained property is a function of position. In some embodiments, the at least one property is selected from a group consisting of conductivity, dielectric constant, and magnetic properties.

In some embodiments, said at least one property is selected from a group consisting of concentration, particle size, particle size distribution, particle shape, dynamic flow characteristics, and water content. In some embodiments, the method also involves identifying inhomogeneous regions in said fluid, and identifying regions of turbulence by the presence of eddies in the velocity field. In some embodiments, the method also involves determining a flow front from said image.

In another aspect, the invention involves a system for analysis of changes in a fluid flowing through a conduit. The system includes a magnetic resonance device, configured to perform imaging of said fluid. The system also includes a processor, configured to allow control of said magnetic resonance device, and processing of magnetic resonance measurements. The system also includes a flow-inducing mechanism, configured to allow generation of flow within the conduit. In some embodiments, the processor is configured to allow processing of data for measuring and monitoring change of at least one property of said fluid, and wherein said property is indexed according to discrete locations for a predetermined coordinate within said conduit.

In some embodiments, the magnetic resonance device is further configured to allow subjection of said fluid to radio frequency signals within a generated magnetic field, and measurement of radio frequency signals re-emitted by said fluid. In some embodiments, the processor is further configured to allow control of the radio frequency wave generation and detection functions.

In some embodiments, the system also includes a computer-readable medium, configured to allow storage of machine instructions for the processor, and also configured to allow storage of information pertaining to the measurement of the radio frequency signals. In some embodiments, the system also includes a visual display for indicating the current state and function of the magnetic resonance device.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, can best be understood by reference to the following detailed description when read with the accompanying drawings in which:

FIG. 1A shows a flow chart for a method of measuring and monitoring physical or chemical properties of a fluid flowing in a conduit, according to some embodiments of the invention;

Figure 1B:
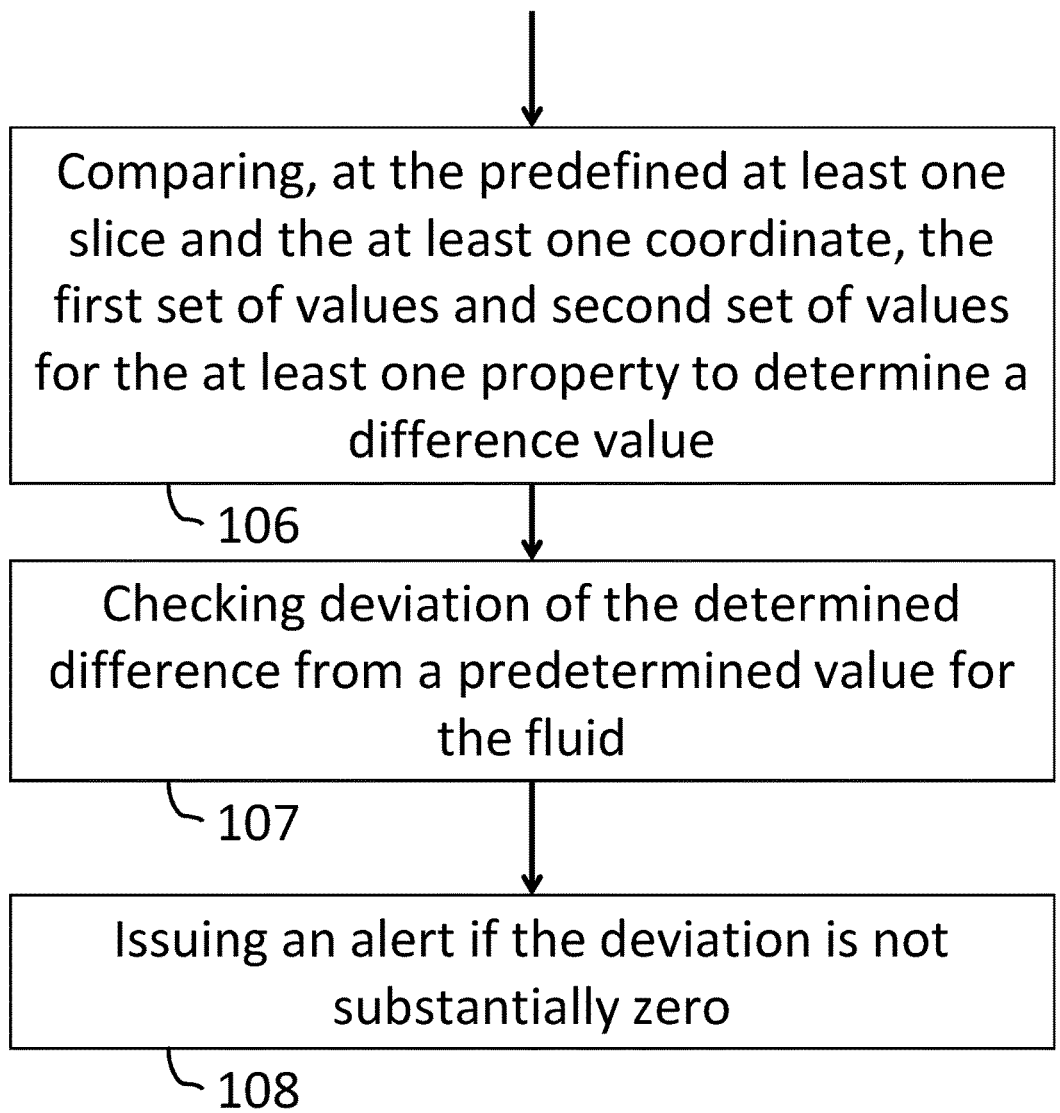
FIG. 1B shows continuation of the flow chart for a method of measuring and monitoring physical or chemical properties of a fluid flowing in a conduit from FIG. 1A, according to some embodiments of the invention.

It will be appreciated that, for simplicity and clarity of illustration, elements shown in the figures have not necessarily been drawn to scale. For example, the dimensions of some of the elements can be exaggerated relative to other elements for clarity. Further, where considered appropriate, reference numerals can be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention can be practiced without these specific details. In other instances, well-known methods, procedures, and components have not been described in detail so as not to obscure the present invention.

Various modifications, however, will remain apparent to those skilled in the art, since the generic principles of the present invention have been defined specifically to provide a non-invasive, means for measuring and controlling, at high precision, physical and/or chemical state transformation of a fluid substance in an industrial environment.

Magnetic measurements (e.g. nuclear magnetic resonance or, magnetic resonance imaging) can be important tools for research and/or development of products and/or processes. For example, in the oil industry, rheological and/or compositional properties of drilling fluids, magnetic measurements can provide essential information for process control. This information can result in real time process changes. For example, in the composition of the drilling fluids, and/or in drilling parameters such as drilling speed and/or weight-on-bit. Given the nature of oilfield drilling operations, such control decisions can have financial ramifications, for example, in the tens of millions of dollars. It therefore can be advantageous to improve analysis of fluids flowing in conduits in order to derive various parameters.

In general, a fluid flowing through a conduit can be magnetically measured, e.g., via a magnetic resonance imaging system. A velocity profile can be determined based on the magnetic measurements. A flow profile can be determined based on the velocity profile. Physical and/or chemical properties of the flow fluid can be derived from the flow profile.

Reference is now made to FIGS. 1A-1B, which show a flow chart for a method of measuring and monitoring a fluid flow in a conduit subjected to magnetic resonance, according to some embodiments of the invention. The method involves defining at least one region of interest within the conduit, and defining 101 at least one coordinate within the region of interest within the conduit. FIG. 1B shows continuation of the flow chart for a method of measuring and monitoring physical or chemical properties of a fluid flowing in a conduit from FIG. 1A.

The at least one coordinate, 'c', can be defined based on a region of interest (ROI) at the conduit (e.g., coordinate defined for slice 500, as shown below in FIG. 5). The ROI can include a first plurality of slices, 'p'. In some embodiments, the ROI can be a selected subset of regions in conduits. The fluid within the conduit can be measured and/or analyzed, for example, by determining one or more of fluid's properties for a selected region of the conduit. The RIO can be a cross-section of the conduit or a volume of interest within the conduit (e.g., for two-dimensional or three-dimensional analysis, respectively).

In some embodiments, the coordinate, 'c', is received from user input, from a file, or any combination thereof. In some embodiments, the coordinate, 'c' is based on an expected fluid flow type. In some embodiments, the coordinate, 'c' is based on a strength of a magnetic field emitted by the magnetic resonance device that provides the magnetic resonance.

In some embodiments, measurements of the fluid homogeneity, for example using a magnetic resonance device (MRD), can be carried out. In case that the measured fluid is not homogeneous, there can be asymmetry in the velocity profile. Sedimentation, for example, can be observed under certain flow rate. Inhomogeneity of the fluid can be detected by observing, for example with the MRD the radial distribution of elements within the fluids (e.g., solid particles, emulsions, and/or bubbles). In some embodiments, measurement of air bubbles within the fluid can allow acquiring the shear rates and/or shear stress as a function of flow rate.

In some embodiments, fluctuations in the measured velocity profile, for example from the magnetic resonance image, can be indicative of conduit fluctuations and therefore allow detection of plugs in the pipe line. For example, calculating detecting fluctuations in cross-sections of a conduit using pressure sensors.

In various embodiments, the at least one coordinate, 'c', is one-dimensional, two-dimensional or three-dimensional.

The method also involved receiving 102 at least one known value for at least one property of the fluid, for at least one slice of the plurality of slices and for the at least one defined coordinate, 'c' 101. In some embodiments, the at least one known value is received from a database of fluid properties and/or received from the user. In some embodiments, the at least one known value is obtained by magnetically measuring a flow fluid having known properties that are substantially identical to desired properties for the flow fluid. For example, the measurements of the flow fluid having known properties can be performed off-line. The at least one known value can be determined based on the magnetic measurements, for example, as is described in EQNs. (1)-(3) below.

In some embodiments, the at least one property is a material property of the fluid flowing through the conduit. In various embodiments, the material property is a material concentration and/or identification of the material type. In some embodiments, the at least one property is a characteristics of the material (e.g., particle size, particle structure, particle shape, dynamic flow characteristics, and/or water content). In some embodiments, the at least one property is an electrochemical transformation of the fluid flowing in the conduit (e.g., changes in the conductivity, dielectric constant, and/or magnetic properties of the fluid flowing in the conduit).

The method also involves, measuring 103 the fluid using magnetic resonance. The magnetic resonance can be provided via a magnetic resonance imaging device, a nuclear magnetic resonance imaging device, and/or any device capable of taking measurement via magnetic resonance, as is known in the art.

The method also involves, determining 104 at least one image from the measured fluid, wherein the at least one image can have a second plurality of slices for the at least one coordinate.

In some embodiments, the second plurality of slices can be equal to the first plurality of slices. For example, the first plurality of slices can be based on the coordinate, 'c'. The second plurality of slices can be based on the measurements obtained by a magnetic resonance device. The magnetic resonance device performing the measurements can attempt to obtain magnetic measurements at the coordinate, 'c', such that the second plurality of slices are equal to the first plurality of slices. In some embodiments, the obtained magnetic measurements are in the exact location of the coordinate, 'c', thus the first plurality of slices and the second plurality of slices are substantially equal. In some embodiments, the obtained magnetic measurements are not in the exact location of the coordinate, 'c', thus the first plurality of slices and the second plurality of slices are not substantially equal. In some embodiments, a determination as to whether the second plurality of slices are sufficiently similar to the first plurality of slices is made. In these embodiments, if sufficiency is found, then the second plurality of slices are used, otherwise, the magnetic measurement can be retaken and/or an alert can issue.

The method also involves determining 105, from the at least one image, a second set of values for the at least one property of the fluid in at least one slice of the second plurality of slices for the at least one coordinate. The second set of values can be determined based on a velocity profile of the fluid flowing through the conduit. The velocity profile can be based on the at least one image.

In various embodiments, a magnetic resonance device that obtains the at least one image uses time-of-flight and/or phase-encoding imaging. In either case, the fluid flowing through the conduit can be exposed to a constant (or substantially constant) magnetic field of a substantially known strength, with a substantially known spatial variation. After spin systems of the magnetic resonance device align with the imposed magnetic field, the spin molecules can be disturbed by a radio-frequency pulse that tags a region in the fluid flow, using a pulsed field gradient spin-echo technique (e.g., as is known in the art).

The time-of-flight imaging can involve selective exciting and/or refocusing of RF pulses emitted during imaging, to selectively affect plane(s) oriented in orthogonal directions in space relative to the fluid flow. These planes can include a region of excitation that is perpendicular to the fluid flow, and then refocusing the excitation to a region that is parallel to and including the flow. The positions of the sources of the resulting spin echoes are imaged, showing a displacement equal to the product of the velocity and the echo time. These images can show the profile of the velocity distribution, both in laminar and non-laminar flows. Phase-encoding imaging can product direct images of velocity profile distributions for both unidirectional and/or more complex flows. In the case of substantially unidirectional (or wholly unidirectional), substantially steady (or wholly steady) flowing fluid, if the position of a nucleus of the flow fluid with a spin at time 't' is $z(t)$, then $z(t)=z_0+wt$, where '$z_0$' is the position of the nucleus of the flow fluid with spin at time zero and 'w' is the velocity of the nucleus with spin. An applied magnetic field gradient in the flow direction, having a magnitude '$g_z$', and the Bloch equations can show that a phase of the magnetization of the flow fluid can be given by:

$$\phi = \gamma_g \int_0^t z(s) g_z(s) ds = \gamma(z_0 m_0 + w m_1) \qquad (1)$$

where '$\gamma_g$' is the gyromagnetic ratio of the nucleus of the flow fluid, and $$m_0 = \int_0^t g_z(s) ds, \quad m_1 = \int_0^t s g_z(s) ds \qquad (2)$$

In phase encode imaging, the applied gradient can be designed such that $m_0=0$ but $m_1 \neq 0$. The phase angle can be proportional to the velocity of the nucleus with spin, such that a gradient of the phase can be used to determine the distribution of velocities in the sample. The rheological property measurements for the region of interest can be based on velocity profiles. This can allow replacing an assumed velocity field by an actually measured profile in analyzing the data for rheological properties of the fluid. The local values of viscosity can be calculated as $$\mu(y) = \tau(y)/\dot{\gamma}(y) \qquad (3)$$

where $\dot{\gamma}(y)$ is the shear rate profile (local shear rate) derived from the measured velocity profile and $\tau(y)$ is the local shear stress obtained either from a pressure difference measurement (capillary or conduit flow geometry) or from a torque measurement (rotational rheometer).

In some embodiments, a reaction can occur during the time that the fluid is flowing within the magnetic resonance device (e.g. NMR). A shape of the velocity profile can characterize the process of the reaction so that corrective feedback can be applied, for example by altering the temperature of the conduit walls, to bring the reaction process within desired parameters.

In some embodiments, the at least one image is magnetic resonance image. The magnetic resonance image can include a three dimensional profile of flow velocity of the fluid flowing (e.g., velocity profile) within the conduit. A determination of flow conditions of the flow fluid can be made based on the velocity profile. The flow conditions can be characterized as laminar, turbulent, and/or transient (between laminar to turbulent) flow.

In some embodiments, at least one of inhomogeneous regions and/or regions of turbulence can be identified in the flowing fluid by the presence of eddies (currents moving in a direction that is different from that of the main current) in the velocity field, as can be determined based on the velocity profile.

In some embodiments, the inhomogeneous regions in the fluid can be selected from a group consisting of gas bubbles, liquid bubbles, regions of stratification, regions of settlement, regions of broken-down emulsion, and regions of incomplete mixing. In some embodiments, a bubble can be at least one region having characteristics which differ significantly from those of the flow of the fluid. Such bubbles can not be substantially spherical or ovoid, but the fluid therein can be of relatively uniform quality. For example, a bubble can be a region of air larger than approximately a millimeter within an emulsion or a liquid, a region of oil within an emulsion or a liquid, and/or a region of liquid within a gas.

The method also involves, comparing 106, at the predefined at least one slice and the at least one coordinate, the first set of value and the second set of values, for the at least one property to determine a difference value. For example, determining a change relative to a predetermined value or threshold.

The method also involves, checking 107 a deviation of the determined difference from a predetermined value for the fluid.

The method also involves, issuing an alert 108 if the deviation is not substantially zero. Otherwise, if the deviation is substantially zero, then in some embodiments, no action is taken.

According to some embodiments, the at least one property that is received can be determined based on that at least one property being measured over a time duration. For example, fluid flowing in a milk pasteurization process can have different behavior over time.

Fluid dynamics indicates that the cross-sectional shape of a conduit can influence the size of its zone of laminar-turbulent flow transition, relative to conduits having other cross-sectional shapes. As such, the combination of magnetic resonance imaging technology with a system of flow conduits specifically chosen for their laminar-turbulent flow transition properties can provide valuable experimental and process control capabilities for determining a fluid's rheological and compositional properties.

In some embodiments, a flow front can be determined from a velocity image and of turbulence can be identified by irregularities in the shape of the flow front.

Figure 2:
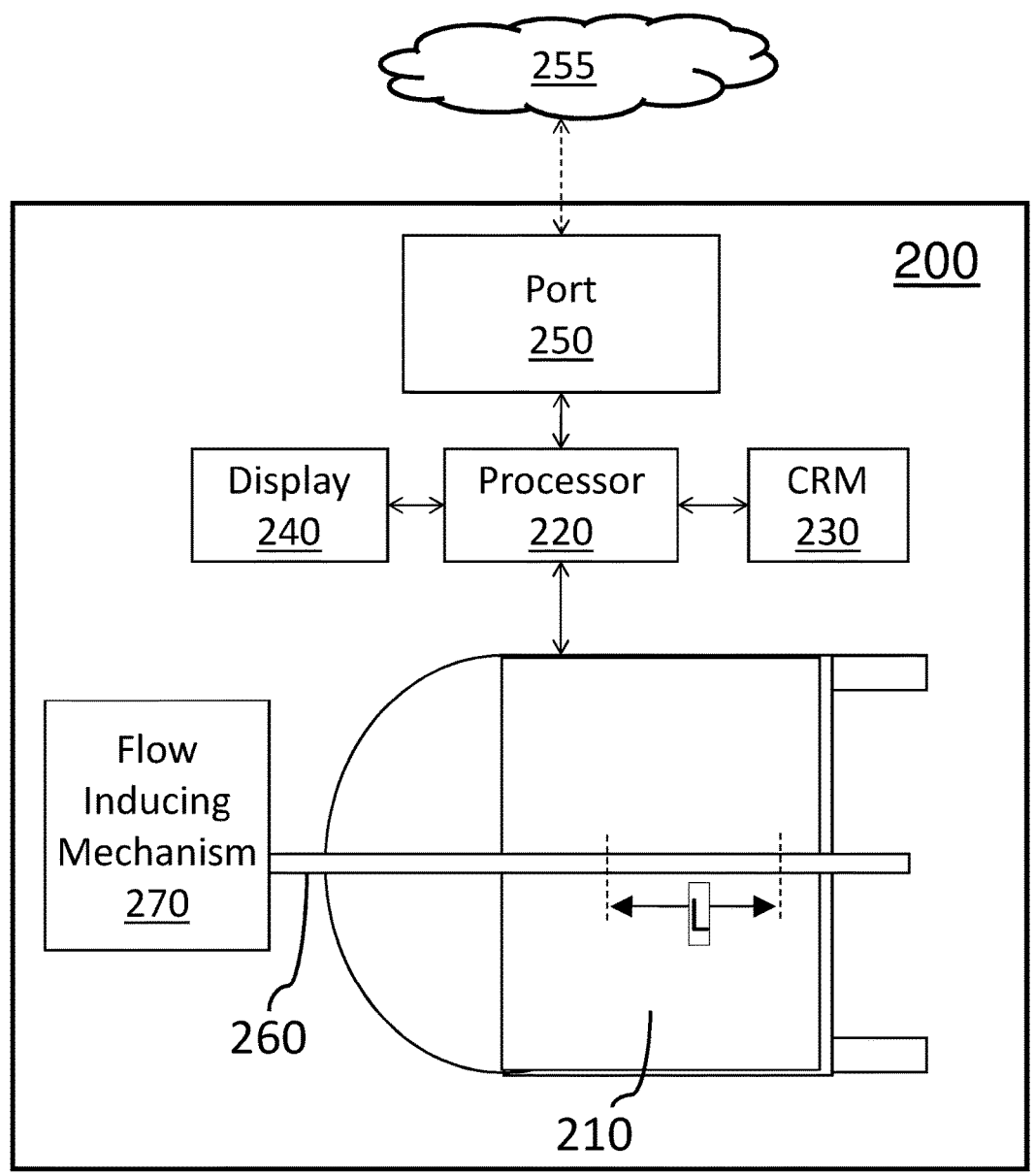
FIG. 2 schematically illustrates a magnetic resonance system for measuring properties of a fluid flowing in a conduit, according to some embodiments of the invention.

Reference is now made to FIG. 2, which schematically illustrates a magnetic resonance system 200 for measuring properties of a fluid flowing in a conduit (with the direction of arrows indicates the direction of information flow), according to some embodiments. The magnetic resonance system 200 can include a conduit 260 that is configured to allow accommodation of the flow of the fluid.

The magnetic resonance system 200 can include a magnetic resonance device 210, such as a NMR spectrometer. The NMR spectrometer can be configured to allow at least one of: subjecting a fluid to radio frequency (RF) signals within a generated magnetic field, measuring RF signals re-emitted by the fluid, and producing an NMR analysed image of the fluid. In some embodiments, the magnetic resonance system 200 can further include a computer processor 220 that is configured to allow control of RF wave generation and detection functions of the magnetic resonance device 210.

According to some embodiments, the magnetic resonance system 200 can further include a computer-readable medium (CRM) 230 for storing machine instructions for the computer processor 220 and/or for storing information pertaining to the measurement and analysing of the RF signals. In some embodiments, the CRM 230 can include computer readable code that when executed causes a plurality of steps to be executed by the computer processor 220 for the analytic processing of data related to the physical properties of the fluid.

In some embodiments, the magnetic resonance system 200 can further include a visual display 240 for indicating the current state and function of the magnetic resonance system 200, for instance the visual display 240 can be a computer screen of a PC. In some embodiments, the magnetic resonance system 200 can further include a digital electronic connection port 250 that is configured to allow digital communication between the magnetic resonance system 200 and a computer communication network 255, for instance the computer communication network 255 can be wired or wireless network such as the Internet.

According to some embodiments, at least one known value for properties of the fluid can be received from user or from the network 255, for at least one slice of the conduit 260. In some embodiments, the known value can be provided for a particular chosen coordinate within the at least one slice of the conduit 260. In some embodiments, the known value can be received from a dedicated database.

According to some embodiments, the magnetic resonance system 200 can further include a flow-inducing mechanism 270 that can be configured to allow flow of the fluids within the conduit 260. In some embodiments, the flow-inducing mechanism 270 can control the velocity of the fluid within the conduit 260.

According to some embodiments, measuring physical properties of a fluid with the magnetic resonance system 200 can include subjecting said fluid to RF signals within a magnetic field generated by the magnetic resonance device 210, measuring RF signals re-emitted by the fluid with the magnetic resonance device 210, and then producing an NMR image of said fluid.

In some embodiments, the conduit can be any of a pipe, a tube, a hose or conduit of fluids (e.g., gasses, liquids, solids, aerosols, emulsions and any mixtures thereof), including conduits of any size, cross-section texture, and shape, flexible conduits, semi-flexible conduits and rigid conduits, partially open channels, conduit's fittings, conduit's add-ons, conduit's joints and forks, conduit's inserts and outwardly fitted means, linear and non-linear conduits, metal-made conduits, polymer-made conduits, glass-made conduits or otherwise-made conduits, and any combination thereof.

In some embodiments, a feedback mechanism can be integrated in the system so if one or more properties of a fluid deviate from the set criterions, a production process can be altered to induce fluid properties to return to the preset criterions. For example, the production process can be altered through change of fluid temperature, pressure etc. In some embodiments, at least one property can be selected from a group consisting of fluid type, fluid density, fluid viscosity, fluid viscoelasticity, fluid yield stress, and any combination thereof In some embodiments, the fluid type can be selected from a group consisting of Newtonian fluid, pseudoplastic fluid, dilatant fluid, Bingham plastic fluid, and Herschel-Bulkley fluid.

In some embodiments, the product can be an emulsion such as milk or mayonnaise Emulsion normally exhibit Herschel-Bulkley type flow, with a characteristic flow profile. If air bubbles occur in the fluid or the emulsion breaks down, the flow profile can become less sharp and symmetric.

Figure 3:
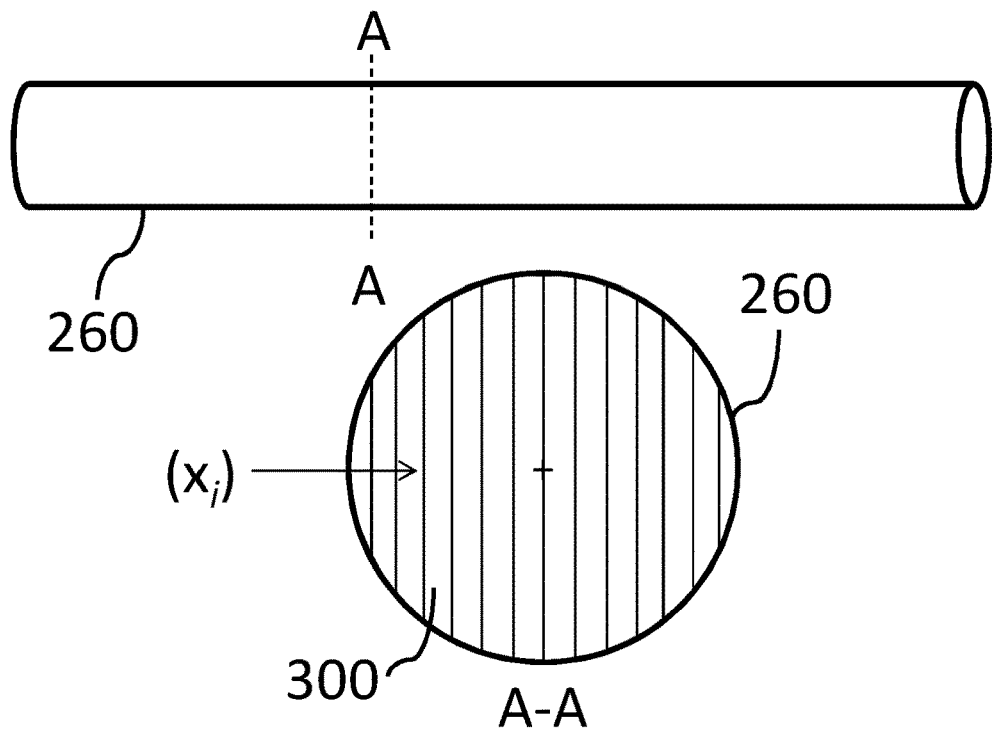
FIG. 3 schematically illustrates indexing a one-dimensional point in a selected cross-section of a fluid flowing in conduit, according to some embodiments of the invention.
Figure 4:
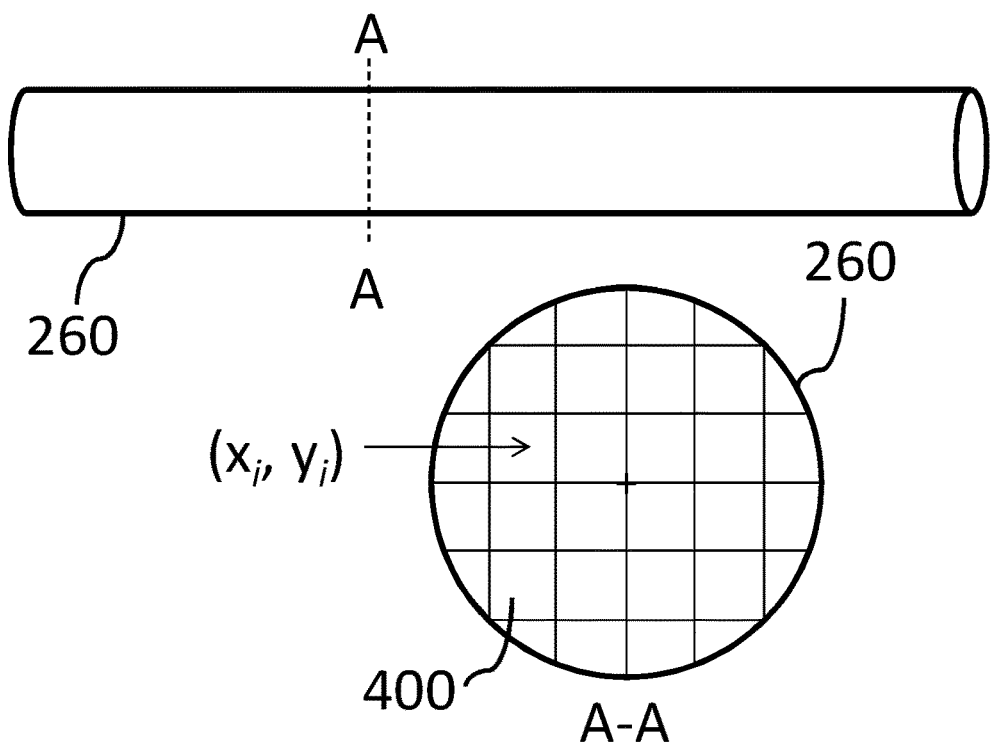
FIG. 4 schematically illustrates indexing a two-dimensional pixel in a selected cross-section of a fluid flowing in conduit, according to some embodiments of the invention.
Figure 5:
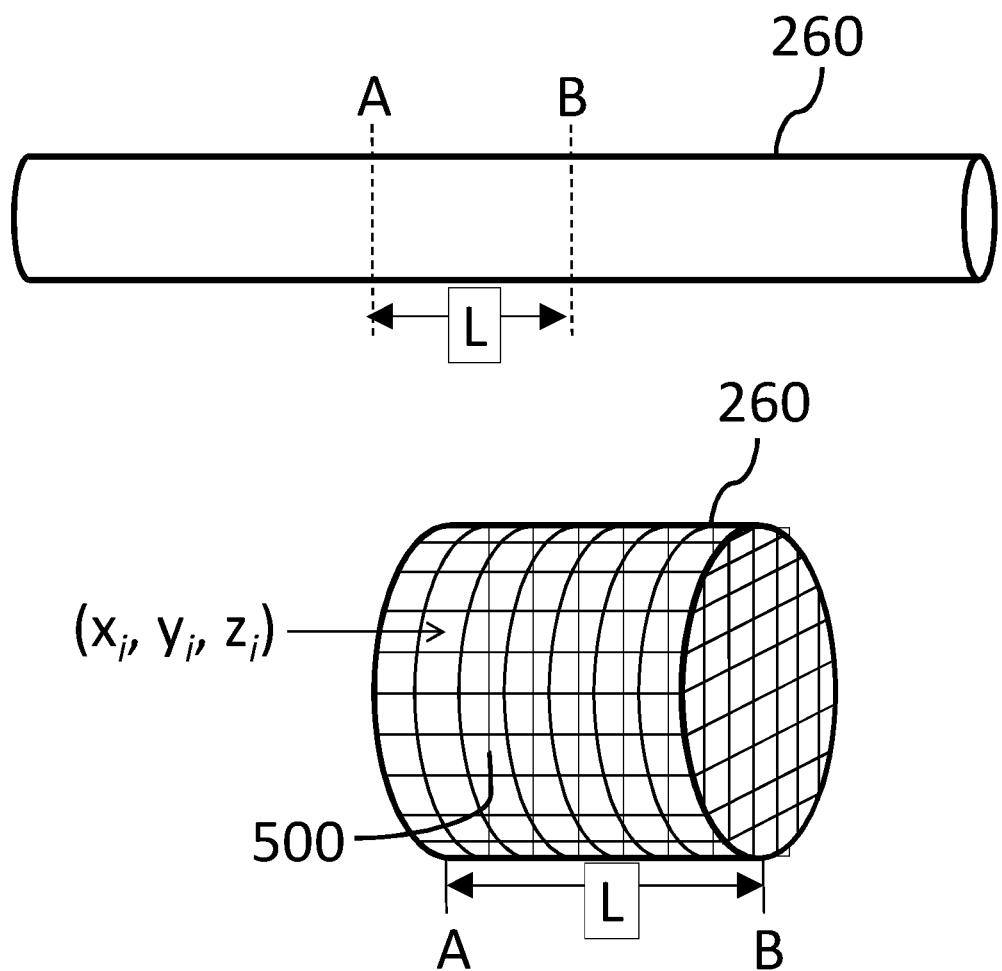
FIG. 5 schematically illustrates indexing a three-dimensional voxel in a volume of interest of a fluid flowing in conduit, according to some embodiments of the invention.

Reference is now made to FIGS. 3-5, which show examples of indexing fluid in a region of interest and mapping fluid properties as a function of location in one-dimensional, two-dimensional and three-dimensional space, respectively. In some embodiments, fluid parameters (e.g. viscosity or temperature) are chosen such that mapping of a fluid front is generated from the velocity profile as a function of position in the region of interest. FIG. 3 schematically illustrates indexing one-dimensional point in a selected cross-section of a fluid flowing in the conduit 260, according to some embodiments of the invention.

A region of interest chosen in the conduit 260 (e.g. as shown in cross-section A-A), can include a plurality of slices 300 of a predetermined width. A one-dimensional coordinate (xi) can be selected within the conduit 260 in order to determine fluid parameters for that coordinate. The selected coordinate (xi) can correspond to the at least one slice 300, such that fluid analysis for the corresponding slice 300 can be performed. In some embodiments, a single coordinate (xi) can correspond to two slices 300, for instance being on the border of these slices, such that measurements can be carried out for all of the corresponding slices 300 to determine the required fluid parameters for the coordinate. In some embodiments, a measurement may be carried out for a plurality of parameters and for a plurality of coordinates, for example receiving a plurality of known values to be compared with measured values at multiple coordinates in the conduit.

FIG. 4 schematically illustrates indexing two-dimensional pixel in a selected cross-section of a fluid flowing in the conduit 260, according to some embodiments of the invention. The term "pixel" can refer to an element in a two-dimensional grid, and the term "voxel" can refer to an element in a three-dimensional grid.

A region of interest chosen in the conduit 260 (e.g. as shown in cross-section A-A), can include a plurality of slices 400 of a predetermined size. A two-dimensional coordinate $(x_i, y_i)$ can be selected within the conduit 260 in order to determine fluid parameters for that coordinate. The selected coordinate $(x_i, y_i)$ can correspond to the at least one slice 400, such that fluid analysis for the corresponding slice 400 can be performed. In some embodiments, a single coordinate $(x_i, y_i)$ can correspond to two slices 400, for instance being on the border of these slices, such that measurements can be carried out for all of the corresponding slices 400 to determine the required fluid parameters for the coordinate.

In some embodiments, the chosen coordinate can be selected from discrete locations within the conduit, such as the plurality of slices.

FIG. 5 schematically illustrates indexing a three-dimensional voxel in a selected cross-section of a fluid flowing in conduit, according to some embodiments of the invention. According to some embodiments, measuring physical properties of a fluid flowing in a conduit, for instance with the magnetic resonance system 200 (as shown in FIG. 2), can include analysing a slice of predefined length, 'L', of the conduit in order to determine the amount of shear stress applied to each layer of fluid therein. Shear stress in the conduit can have substantially linear behaviour as a function of distance along the conduit, such that by measuring the pressure drop between two distant point, having a known distance within the conduit with the magnetic resonance system 200, the shear rate can be determined.

A region of interest chosen in the conduit 260 (e.g. as shown in cross-section A-A), can include a plurality of slices 500 of a predetermined size. A three-dimensional coordinate $(x_i, y_i, z_i)$ can be selected within the conduit 260 in order to determine fluid parameters for that coordinate. The selected coordinate $(x_i, y_i, z_i)$ can correspond to the at least one slice 500, such that fluid analysis for the corresponding slice 500 can be performed. In some embodiments, a single coordinate $(x_i, y_i, z_i)$ can correspond to two slices 500, for instance being on the border of these slices, such that measurements can be carried out for all of the corresponding slices 500 to determine the required fluid parameters for the coordinate.

In some embodiments, a magnetic resonance device (MRD) is configured for measuring and monitoring rheological properties at an oilfield drilling rig site. For example, viscosity of the drilling fluid can be determined. In the petroleum exploration industry, rheological and compositional properties of drilling fluid, circulated down the drilling pipe and back up the annulus of the surrounding borehole can provide essential information for process control. This information can often results in real time process changes in the composition of the drilling fluid or in drilling parameters such as drilling speed and/or weight-on-bit.

In some situations, the circulated drilling fluid's properties can provide information about the geological structural formation. Some geological structures are associated with greater potential for drilling bottom-hole assemblies becoming stuck. When such conditions are detected, special procedures can be employed to prevent the drill string from getting stuck. A stuck drill string can result in millions of dollars of unpredicted operational costs, especially when expensive bottom-hole tools are lost and wasted days of drilling site costs can accumulate.

In some embodiments, an MRD is configured for measuring and monitoring the rheological properties of the fluid flowing in a ketchup production process. The system can be calibrated and adjusted to a resonance frequency associated with a desired ketchup profile. On-line measurement (e.g., measurement functions operational in real time and without a need for human intervention) can be continuously performed on the produced ketchup stream and an alert can be activated if the system detects a fluid viscosity deviation greater than 0.5% from the calibrated viscosity value. Fluid viscosity can be an important parameter to monitor for ketchup, as the consistency of ketchup can be important to a consumer.

The MRD can measure a cross-sectional zone of laminar-turbulent transition within the flow of the ketchup production line. This can be done to isolate and identify any ingredients which have failed to completely assimilate into the fluid matrix. As such, product consistency and/or quality control can be maximized.

In some embodiments, an MRD is configured to measure the properties of the fluid flowing in a milk pasteurization process. The milk can be considered as an emulsion, which can exhibit Herschel-Bulkley type flow, with a characteristic flow profile. If the emulsion breaks down, the flow profile can change to be less sharp and more asymmetric. By monitoring flow profile change, the conditions of milk pasteurization process can be better controlled and thus potential financial damages can be avoided.

In some embodiments, an MRD is configured to measure the blood flow in arteries. The cardiovascular system in human body can be considered as an internal flow circle with multiple branches in which a complex liquid circulates. Normal arterial flow can be laminar with secondary flows generated at curves and branches. The arteries are living organs that can be adapted to and change with the varying hemodynamic (blood flow) conditions. Unusual hemodynamic conditions can create or indicate an abnormal biological response.

Velocity profile skewing can create, for example, pockets in which the direction of the blood vessel (as the conduit) wall's shear stress oscillates. Atherosclerotic disease can be localized in these sites and can result in a narrowing of the artery, such as lumen-a stenosis. The stenosis can cause turbulence and reduce flow by means of viscous head losses and flow choking. Very high shear stresses near the throat of the stenosis can activate platelets and thereby induce thrombosis, which can totally block blood flow to the heart or brain. Detection and quantification of stenosis can serve as the basis for surgical intervention. Analyzing hemodynamic conditions with a three-dimensional, pulsatile flow at the edge of turbulence can provide useful information for diagnosis and/or quantifying diseases.

In some embodiments, the pulp and paper industry can use the complex mixture of high molecular weight compounds from wood pulp as its raw material. NMR can be used to characterize the pulp and/or to determine the effect of different mechanical or chemical treatments of the type of pulp produced. Aqueous pulp suspensions can exhibit non-Newtonian fluid behavior. The Bingham model can be used to provide insight into the observed behavior. Even in conduit flow, while the Bingham model can capture the plug behavior in the center of the conduit, it does not address the important mechanisms at work outside the plug region where unsteady flow occurs. Therefore, by mapping the fluid flow, qualitative comparison of region of interest indicate a microstructure of pulps, which can be helpful for the monitoring of pulp production in the factory.

Unless explicitly stated, the method embodiments described herein are not constrained to a particular order in time or chronological sequence. Additionally, some of the described method elements can be skipped, or they can be repeated, during a sequence of operations of a method.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

Various embodiments have been presented. Each of these embodiments can of course include features from other embodiments presented, and embodiments not specifically described can include various features described herein.

The invention claimed is:

1. A method of analyzing changes in a fluid flowing through a conduit, the method comprising:
    defining at least one coordinate within said conduit, said conduit having a first plurality of slices;
    receiving at least one known value for at least one property of the fluid, for at least one slice of the plurality of slices and for said at least one coordinate;
    measuring said fluid using magnetic resonance;
    determining at least one image from the measured fluid, the at least one image having a second plurality of slices for said at least one coordinate;
    determining, from said image, a second set of values for said at least one property of said fluid in at least one slice of said second plurality of slices for said at least one coordinate;
    comparing, at said predefined at least one slice and said at least one coordinate, the first set of values and second set of values for said at least one property to determine a difference value;
    checking deviation of the determined difference from a predetermined value for said fluid; and
    issuing an alert if the deviation is not substantially zero.

2. The method of claim 1, wherein the at least one coordinate is one-dimensional.

3. The method of claim 1, wherein the at least one coordinate is two-dimensional.

4. The method of claim 1, wherein the at least one coordinate is three-dimensional.

5. The method of claim 1, wherein known values for the at least one property of the fluid are received from at least one of an external database and a user.

6. The method of claim 1, wherein the measuring of said fluid using magnetic resonance is carried out with magnetic resonance imaging.

7. The method of claim 1, wherein the first plurality of slices is equal to the second plurality of slices.

8. The method of claim 1, wherein the first plurality of slices is different from the second plurality of slices.

9. The method of claim 1, wherein at least one coordinate is received from at least one of an external database and a user.

10. The method of claim 1, wherein a plurality of 'c' coordinates is defined, wherein a plurality of 'p' slices is defined, and wherein 'c' and 'p' are integers, each of which is greater than one.

11. The method of claim 1, wherein the obtained property is a function of position.

12. The method of claim 1, wherein said at least one property is selected from a group consisting of conductivity, dielectric constant, and magnetic properties.

13. The method of claim 1, wherein said at least one property is selected from a group consisting of concentration, particle size, particle size distribution, particle shape, dynamic flow characteristics, and water content.

14. The method of claim 1, further comprising identifying inhomogeneous regions in said fluid, and identifying regions of turbulence by the presence of eddies in the velocity field.

15. The method of claim 1, further comprising determining a flow front from said image.

16. A system for analysis of changes in a fluid flowing through a conduit, the system comprising:
    a magnetic resonance device, configured to perform imaging of said fluid;
    a processor, configured to allow control of said magnetic resonance device, and processing of magnetic resonance measurements; and
    a flow-inducing mechanism, configured to allow generation of flow within the conduit,
    wherein the processor is configured to allow processing of data for measuring and monitoring change of at least one property of said fluid, and wherein said property is indexed according to discrete locations for a predetermined coordinate within said conduit.

17. The system of claim 16, wherein the magnetic resonance device is further configured to allow subjection of said fluid to radio frequency signals within a generated magnetic field, and measurement of radio frequency signals re-emitted by said fluid.

18. The system of claim 16, wherein the processor is further configured to allow control of the radio frequency wave generation and detection functions.

19. The system of claim 18, further comprising a computer-readable medium, configured to allow storage of machine instructions for the processor, and also configured to allow storage of information pertaining to the measurement of the radio frequency signals.

20. The system of claim 16, further comprising a visual display for indicating the current state and function of the magnetic resonance device.

* * * * *